United States Patent
Franken-Stellamans et al.

(10) Patent No.: US 7,339,084 B2
(45) Date of Patent: Mar. 4, 2008

(54) METHOD FOR THE PRODUCTION OF ACETALDEHYDE FROM ETHYLENE AND OXYGEN

(75) Inventors: Erhard Franken-Stellamans, Niedernhausen (DE); Mario Fähtz, Villmar (DE); Klaus Hett, Bad Homburg (DE)

(73) Assignee: Celanese Chemicals Europe GmbH, Oberhausen (DE)

( * ) Notice: Subject to any disclaimer, the term of this patent is extended or adjusted under 35 U.S.C. 154(b) by 0 days.

(21) Appl. No.: 11/657,759

(22) Filed: Jan. 25, 2007

(65) Prior Publication Data

US 2007/0208203 A1 Sep. 6, 2007

(30) Foreign Application Priority Data

Jan. 28, 2006 (DE) .................. 10 2006 004 074

(51) Int. Cl.
*C07C 45/27* (2006.01)
*C07C 45/34* (2006.01)

(52) U.S. Cl. ..................... 568/470; 568/475

(58) Field of Classification Search .............. None
See application file for complete search history.

(56) References Cited

U.S. PATENT DOCUMENTS 6,140,544 A * 10/2000 Rinne et al. ............ 568/475
6,478,851 B2 * 11/2002 Berwe et al. ............ 95/45
2002/0087032 A1   7/2002 Berwe

FOREIGN PATENT DOCUMENTS

DE           25 21 092 A1    11/1976
JP           2003002860 A    8/2003

OTHER PUBLICATIONS

Ullmann 1974 "Acetaldehyd" Band 7 pp. 18-19.

* cited by examiner

*Primary Examiner*—Sikarl A. Witherspoon
(74) *Attorney, Agent, or Firm*—Charles A. Muserlian

(57) ABSTRACT

A single-stage method for the oxidation of ethylene to acetaldehyde in the presence of an aqueous catalyst solution comprising copper chloride and palladium chloride under maintenance of the circulation of the aqueous catalyst solution in a recycle reactor, comprised of a reactor and a mist trap and which includes an externally applied thermal insulation.

8 Claims, No Drawings

METHOD FOR THE PRODUCTION OF ACETALDEHYDE FROM ETHYLENE AND OXYGEN

The present invention relates to a single-stage method for the oxidation of ethylene to acetaldehyde in the presence of an aqueous catalyst solution by means of improved thermal insulation in a recycle reactor.

STATE OF THE ART

It is known to oxidize ethylene or other olefins, such as propylene, butylene or isobutylene, with oxygen or gases containing oxygen to aldehydes, ketones or to acids corresponding to the aldehydes. The conversion takes place in water in the presence of inert metals of groups VIII of the periodic system of elements or their salts, which form complex compounds with the olefins, and redox systems (DE 11 90 451).

The oxidation of ethylene to acetaldehyde has attained large-scale commercial significance. For the catalysis of the strongly exothermic oxidation reaction with oxygen as the oxidation agent, an aqueous hydrochloric acid solution of copper chloride and palladium chloride is conventionally employed. In principle, the reaction process can be divided into two partial steps. In the so-called ethylene reaction, the formation of acetaldehyde from ethylene and water takes place in homogeneous catalysis in the presence of a palladium (II) chloro complex, which disintegrates under the formation of elementary palladium, which is re-oxidized to palladium with the oxidations stage +II through the copper (II) chloride also present. The copper(I) chloride formed is subsequently oxidized in the so-called oxidation reaction with oxygen in hydrochloric acid solution to copper(II) chloride, which subsequently is active again in the ethylene reaction.

In the technical design of acetaldehyde production, two variants of the method have evolved. In the single-stage method, the ethylene reaction and the oxidation reaction occuring the same reactor, while according to the two-stage method, the ethylene reaction and the oxidation reaction proceed in separate reactors. However, this two-stage variant of the method requires a catalyst circulation entailing high energy consumption and has technically been less frequently realized than the single-stage variant. The ethylene reaction and oxidation reaction proceeding in the single-stage method variant in one reactor vessel will be combined in the following under the term "ethylene oxidation" to describe the acetaldehyde formation in the reaction vessel.

In the case of the single-stage method, a so called recycle reactor has been found to be a suitable reaction vessel. Recycle reactors are reaction vessels conventionally used in chemical process engineering. They are counted among the static reaction vessels and in them, the thorough mixing with back-mixing takes place due to the convection flow caused by the heat of reaction. The recycle reactor utilized in the industrial production of acetaldehyde through ethylene oxidation can, in principle, be described as an arrangement of two reaction vessels connected with one another by tubing, with one reaction vessel operating as the reactor and the other as a mist trap. Between the reactor and the mist trap, a forced circulation of the liquid catalyst is maintained. The energy required for this purpose is supplied for one by the heat of reaction of the strongly exothermic ethylene oxidation and, for another, the gases ethylene, oxygen and the recirculated cycle gas fed into the reactor also drive the forced catalyst circulation. The reaction is carried out under pressure and at the boiling point of the reaction mixture, wherein the pressure is adjusted via the ethylene input depending on the facility utilization. The associated boiling temperature, and therewith also the reaction temperature, in the reactor follows as a function of the preset pressure. The heat of reaction is utilized for driving the forced catalyst circulation and, above that, is dissipated by evaporation of acetaldehyde and water. The reactor is consequently operated under hot cooling. In addition to the forced catalyst circulation taking place between reactor and mist trap, a forced catalyst circulation is also maintained in the reactor itself through convection flow.

The generated reaction mixture, comprising substantially the aqueous catalyst solution, water vapor, gaseous acetaldehyde and mist from the aqueous catalyst solution, flows over into the mist trap in which the acetaldehyde-containing process gases evaporate. The aqueous catalyst solution as well as condensed water vapor and mist are subsequently circulated back into the reactor. As already described, the driving force for this recirculation is the heat of reaction or the kinetic energy of the fed-in gases.

OBJECTS OF THE INVENTION

It is an object of the invention to provide a single-stage method for oxidation of ethylene to acetaldehyde in the presence of an aqueous catalyst solution.

This and other objects and advantages of the invention will become obvious from the following detailed description.

THE INVENTION

It has unexpectedly been found that the catalyst selectivity, and therewith the space-time yield, in the ethylene oxidation can be improved if the catalyst circulation in the recycle reactor is increased. Improvement of the space-time yield leads to an increase in the capacity of the existing acetaldehyde production facility without additional expensive investment costs or it means a lower system pressure and, associated therewith, a lower reaction temperature at constant productivity. A lower reaction temperature, however, entails an improved catalyst selectivity, such that fewer gaseous byproducts, for example carbon dioxide, as well as fewer water-soluble byproducts, such as acetic acid, accumulate.

The present invention therefore relates to a single-stage method for the oxidation of ethylene to acetaldehyde in the presence of an aqueous catalyst solution comprised of a solution of copper chloride and palladium chloride under maintenance of the circulation of the aqueous catalyst solution in a recycle reactor composed of a reactor and a mist trap, wherein the entire recycle reactor includes an externally applied thermal insulation.

The space-time yield of acetaldehyde in the ethylene oxidation can unexpectedly be improved through a marked increase of the thermal insulation of the recycle reactor. Without wishing to enter into mechanistic considerations, it may be supposed that improved thermal insulation raises the rate of circulation of the aqueous catalyst solution and thus ensures greater stationary concentrations of copper(II) chloride in the ethylene conversion zone of the recycle reactor. A higher concentration of copper(II) chloride, in turn, generates a higher concentration of palladium(II) complexes, at which the actual conversion of ethylene and water to acetaldehyde takes place.

As a possible measure for increasing the circulation rate of the aqueous catalyst solution in the recycle reactor may be considered an increase of the cycle gas quantity. By cycle gas is understood the gas stream accumulating during the processing of the reaction mixture to unprocessed acetaldehyde, which stream, after the separation of acetaldehyde and outward transfer of a discharge gas stream containing inert substances, is cycled back into the reactor portion. While an increase of the cycle gas quantity, on the one hand, causes an increase of the circulation rate of the aqueous catalyst solution in the recycle reactor, it does, however, entail many disadvantages. Increased cycle gas operation leads to an increased loading of the cycle gas compressor, which is tied to greater expenditure of compression energy. Under increased loading in the cycle gas washer, the quantity of washing water must also be increased, which collects in the unprocessed acetaldehyde and must be separated again with the expenditure of energy. An increase of the cycle gas quantity also leads to increased droplet removal of aqueous catalyst solution from the reactor and therewith to losses of the inert metal. The increased input of the cooled cycle gas, lastly, also leads to an abstraction of the heat of reaction, since the cooled and input cycle gas must be heated again.

A decisive and unexpected measure for increasing the circulation rate of the aqueous catalyst solution in the recycle reactor has been found to be improved thermal insulation of this recycle reactor. The heat loss due to the natural convection of the moved air encompassing the recycle reactor and due to the heat radiation from the reactor surface is thereby decreased. As a consequence of the improved thermal insulation, a greater proportion of the released heat of reaction remains in the reaction system and leads to increased evaporation of the water which serves as a solvent for the copper and palladium salts. A higher evaporation rate of the water leads to an amplification of the density differences between the reactor content and the mist trap content, from which subsequently results a rise in the circulation rate of the aqueous catalyst solution. According to the inventive operating method, in the final analysis, the heat of reaction of the strongly exothermic ethylene oxidation reaction is consequently utilized via the improved catalyst circulation for a selectivity improvement for the reaction leading to the desired acetaldehyde.

As a further effect which results due to the improved thermal insulation of the recycle reactor, a rapid removal of the formed acetaldehyde from the reaction zone due to enhanced evaporation is observed. The stationary concentration of the acetaldehyde in the reaction mixture is thereby lowered and the formation of byproducts, which are based on the undesired subsequent reaction of the formed acetaldehyde in the reactor, can be reduced.

In the selection of suitable materials for the recycle reactor, which permit the improvement of the thermal insulation, the aggressive properties of the aqueous catalyst solution as well as the temperature loading due to the high heat of reaction, which, in general, is in a range from 110 to 140° C., must be taken into consideration. Due to its content of hydrochloric acid as well as due to the dissolved palladium and copper chlorides, the aqueous catalyst solution has extremely corrosive properties with respect to the metallic apparatus materials.

The recycle reactors, conventionally utilized in carrying out the single-stage method for the formation of acetaldehyde and composed of a reactor part and a mist trap, are fabricated from carbon steel customary in chemical apparatus engineering. The carbon steel is rubberized in the inside for the purpose of corrosion protection. To protect the rubber lining against the high reaction temperatures, a multi-layered acidproof, ceramic lining is applied on this rubber lining. Since the acidproof ceramic lining has a relatively high thermal conductivity, by necessity a considerably heat loss and heat elimination through the wall of the entire recycle reactor toward the outside results. Conventional recycle reactors therefore also have a relatively high external surface temperature of approximately 70° C. Consequently, based on this layout of the reactor, a temperature gradient is formed across the container wall which, however, is also desired to ensure that the rubber lining is not heated above its decomposition temperature of approximately 80° C.

The significantly improved thermal insulation for carrying out the method of the invention cannot be attained in recycle reactors of conventional layout, since an improvement of the internal insulation of the reactor requires the employment of a material which is acidproof as well as also highly heat insulating and can be applied on the rubber lining. Such materials are not available cost-effectively, and their use as reactor material would so increase the investment costs that it would no longer be possible to operate the acetaldehyde production process economically. The application of an effective outer insulation is not possible in conventional recycle reactors, since this measure leads to the overheating of the rubber layer applied on the inside.

The method of the invention for the production of acetaldehyde is characterized by being carried out in a recycle reactor made of a material, or several material layers, permitting an effective external thermal insulation.

In an embodiment of the method of the invention, the pressure-bearing part of the recycle reactor may be made of a material which is corrosion-resilient against the aqueous catalyst solution, for example of titanium, tantalum or niobium-zirconium alloys, preferably of titanium.

In a further embodiment of the method of the invention, for the pressure-bearing part of the recycle reactor the utilization of conventional, non-corrosion resistant materials, such as for example carbon steel or customary special steels, is also possible provided the inner reactor wall is coated with a corrosion-stable material, which simultaneously has adequate temperature stability at the reaction temperature. For such coating applied on the inside are suitable for example, coating of enamel or of special polyhalogenated hydrocarbons.

The thermal insulation applied externally onto the recycle reactor is comprised of a material conventionally used for thermal insulation with adequate temperature stability at the reaction temperature of the acetaldehyde formation. Examples of such thermally insulation materials are mineral fibers or glass gall. The external thermal insulation is advisably applied in such thickness that the temperature on the reactor surface matches that of the environment. The material employed for the external thermal insulation is generally applied in a thickness of up to 100 mm. A further application beyond that of the thermally insulating materials does not yield a further improvement and makes the method unnecessarily expensive.

The improved thermal insulation improves the catalyst circulation in the recycle reactor whereby a higher concentration of catalytically active metal salts can be set in the ethylene conversion zone. Thereby, in turn, the space-time yield of acetaldehyde can be improved. Due to the improved thermal insulation, the formed acetaldehyde also evaporates more rapidly from the hot reaction zone and the formation of byproducts can be reduced.

Depending on the facility demand, i.e. depending on the quantity of ethylene introduced hourly into the recycle reactor, the specific discharge gas accumulation per ton of ethylene can be reduced. Entailed in a reduction of the discharge gas accumulation, which is essentially given by a low carbon dioxide formation due to the improved catalyst selectivity, is a decrease of the formation rates of other byproducts, for example of acetic acid, which are transferred out of the process by way of the waste water. Therewith, the loading of the outward-transferred waste water with organic contaminants can also be reduced. Improved catalyst selectivity permits an increase of the facility capacity at constant reaction conditions, or, if a specific production capacity or the maximum load are to be processed, carrying out the conversion under reduced facility pressure. Due to the low accumulation of byproducts, the selectivity gain tied to these mild reaction conditions leads to a significant increase in the yield of acetaldehyde.

A further observed effect is that the content of copper(I) chloride in the total copper content in the aqueous catalyst solution depends only marginally on the ethylene intake and lies at a markedly lower level. The improved thermal insulation of the recycle reactor and the improved catalyst circulation determined thereby causes the copper(I) oxide formed in the course of the reaction to be very rapidly transported again into the region of the oxygen feeding and to be re-oxidized here to copper(II) chloride. The ethylene intake which corresponds to the facility capacity therefore has now only a small effect onto the stationary concentration of copper(I) and copper(II) chloride in the entire reaction system.

In the following example, there is illustrated a preferred embodiment of the method to illustrate the same. However, it should be noted that the invention is not intended to be limited to the specific embodiment.

EXAMPLE

In a recycle reactor made of titanium and composed of a reactor and a mist trap, through connection lines, the boiling gas/liquid mixture is conducted from the reactor into the mist trap, from which the aqueous catalyst solution flows back into the reactor via the bottom. The product stream evaporating from mist trap in gaseous form is carried off and cooled in the heat exchangers under condensation. The condensate accumulating after the heat exchanger is removed and mixed with make-up water. The mixture is placed onto the head of the mist trap, which flows in counter flow toward the product stream evaporating from the liquid reaction mixture. The stream of gas and condensate accumulating after the heat exchanger is placed onto the lower part of a wash column, from which unprocessed acetaldehyde is carried off and processed according to methods known per se.

From the gaseous product removed at the head of the wash column, a waste gas stream containing inter alia inert substances is transferred out, while the remainder is recycled as cycle gas, is compressed in the compressor and mixed with fresh ethylene supplied. The gas mixture is subsequently input at that site into the bottom of the reactor, at which the aqueous catalyst solution transported also enters the reactor. Fresh oxygen is sprayed through nozzles into the bottom of the reactor. The lower part of the reactor can therefore also be considered as the oxidation zone for the re-oxidation of copper(I) to copper(II) chloride. The convection flow taking place in the reactor as well as the forced circulation taking place in the mist trap, is also depicted schematically. The evaporation of the aldehyde-containing reaction products from the reaction solution occurring in the mist trap is also schematically indicated.

Operational Experience

In a commercial industrial facility for the production of acetaldehyde from ethylene and oxygen, the recycle reactor laid out with a conventional ceramic lining was replaced by one such fabricated of titanium, which was covered with an external thermal insulation of 100 mm of mineral fibers. The other dimensions of the apparatus remained exactly the same. As a result, due to this measure within the customary load range of 3.2 to 6.1 t/h of ethylene, a reduction by 60 to 70% of the specific waste gas formation was observed depending on the facility load. Within this load range, a decrease of the CSB discharge (chemical oxygen requirement) via the operating waste water of on average 0.55 t/d were also noted. The total yield of the acetaldehyde facility could be increased by approximately 1% relative to the ethylene input. To achieve the previous ethylene intake, the acetaldehyde facility operated according to the inventive method can now be operated at a lower facility pressure which is approximately 10% lower than that according to the conventional working method.

Various modifications of the method of the invention may be made without departing from the spirit or scope thereof. It is to be understood that the invention intended to be limited only as defined in the appended claims.

What we claim is:

1. A single-stage method for the oxidation of ethylene to acetaldehyde in the presence of an aqueous catalyst solution comprising oxiding ethylene in a solution of copper chloride and palladium chloride under maintenance of circulation of the aqueous catalyst solution in a recycle reactor composed of a reactor and a mist trap, wherein the entire recycle reactor includes an externally applied thermal insulation to form acetaldehyde.

2. The method of claim 1, wherein the externally applied thermal insulation to the reactor has a thickness of up of 100 mm.

3. The method of claim 1, wherein the externally applied thermal insulation is comprised of a material, which at the reaction temperature of the acetaldehyde formation, has adequate temperature stability.

4. The method of claim 3, wherein the externally applied thermal insulation is mineral fibers or glass gall.

5. The method of claim 1, wherein a pressure-bearing part of the recycle reactor is made of a material which is corrosion resistant against the aqueous catalyst solution.

6. The method of claim 5, wherein the corrosion-resistant material is selected from the group consisting of titanium, tantalum and niobium-zirconium alloys.

7. The method of claim 1, wherein the pressure-bearing part of the recycle reactor is made of carbon steel or special steels and the inner reactor wall is coated with a corrosion-stable material which simultaneously has adequate temperature stability at the reaction temperature.

8. The method of claim 7, wherein the corrosion-stable and simultaneously temperature-resistant coating is enamel or polyhalogenated hydrocarbons.

* * * * *